United States Patent [19]
Kaplan

[11] 4,197,253
[45] Apr. 8, 1980

[54] CATALYTIC PROCESS FOR PRODUCING POLYHYDRIC ALCOHOLS

[75] Inventor: Leonard Kaplan, Charleston, W. Va.

[73] Assignee: Union Carbide Corporation, New York, N.Y.

[21] Appl. No.: 920,828

[22] Filed: Jun. 30, 1978

[51] Int. Cl.$^2$ ............................................. C07C 27/06
[52] U.S. Cl. ............................... 260/449 L; 260/449.5;
    252/431 C; 252/431 N; 252/431 P; 252/437
[58] Field of Search ............. 260/449 R, 449 C, 449.5

[56] References Cited
U.S. PATENT DOCUMENTS

| 3,944,588 | 3/1976 | Kaplan | 260/449 L |
| 3,954,877 | 6/1976 | Gipson | 568/909 |
| 4,115,433 | 9/1978 | Cosby et al. | 260/449 C |

FOREIGN PATENT DOCUMENTS 2643913  3/1977  Fed. Rep. of Germany ...... 260/449 R

Primary Examiner—Howard T. Mars
Attorney, Agent, or Firm—Marylin Klosty

[57] ABSTRACT

This invention relates to the manufacture of polyhydric alcohol(s) by the reaction of synthesis gas in the presence of a rhodium carbonyl complex catalyst and a phosphine oxide compound.

37 Claims, 2 Drawing Figures

FIG. 1

FIG. 2

CATALYTIC PROCESS FOR PRODUCING POLYHYDRIC ALCOHOLS

This invention relates to an improved process for the manufacture of polyhydric alcohols, in particular alkane polyols, as well as a variety of other chemicals, in particular methanol, from synthesis gas, i.e., a mixture of carbon monoxide and hydrogen.

Specifically, this invention is directed to an improved process of making alkane diols, triols, tetraols, etc., containing 2, 3, 4 or more carbon atoms. A key product of the process of this invention is ethylene glycol. By-products of this invention are the lesser valuable, but nonetheless valuable, monohydric alkanols such as methanol and ethanol. The products of the process of this invention contain carbon, hydrogen and oxygen.

There are described in U.S. Pat. No. 3,833,634, issued Sept. 3, 1974 and U.S. Pat. No. 3,957,857, issued May 18, 1976, processes for reacting hydrogen and oxides of carbon in the presence of rhodium carbonyl complex catalysts. The conditions employed in those processes involve reacting a mixture of an oxide of carbon and hydrogen with a catalytic amount of rhodium in a complex combination with carbon monoxide in a homogeneous liquid phase mixture, at a temperature of between about 100° C. to about 375° C. and a pressure of between about 500 psia and about 50,000 psia. In addition to the aforementioned U.S. Patents, the following U.S. patents and patent applications amplify the development of the process for making alkane polyols from mixtures of hydrogen and oxides of carbon:

U.S. Pat. No. 3,878,292 patented Apr. 15, 1975
U.S. Pat. No. 3,878,290 patented Apr. 15, 1975
U.S. Pat. No. 3,878,214 patented Apr. 15, 1975
U.S. Pat. No. 3,886,364 patented May 27, 1975
U.S. Pat. No. 3,940,432 patented Feb. 24, 1976
U.S. Pat. No. 3,929,969 patented Dec. 30, 1975
U.S. Pat. No. 3,952,039 patented Apr. 20, 1976
U.S. Pat. No. 3,948,965 patented Apr. 6, 1976
U.S. Pat. No. 3,944,588 patented Mar. 16, 1976
U.S. Pat. No. 3,957,857 patented May 18, 1976
U.S. Pat. No. 3,968,136 patented July 6, 1976
U.S. Pat. No. 3,974,259 patented Aug. 10, 1976 (formerly U.S. Ser. No. 455,380, filed Mar. 27, 1974)
U.S. Pat. No. 3,989,799 patented Nov. 2, 1976 (formerly U.S. Ser. No. 455,379, filed Mar. 27, 1974)
U.S. Pat. No. 4,013,700 patented Mar. 22, 1977 (formerly U.S. Ser. No. 526,942, filed Nov. 25, 1974)
U.S. Ser. No. 488,139 filed July 12, 1974 (now abandoned)
U.S. Ser. No. 506,862 filed Sept. 17, 1974 (now abandoned)
U.S. Pat. No. 4,001,289 patented Jan. 4, 1977 (formerly U.S. Ser. No. 506,864, Filed Sept. 17, 1974)
U.S. Ser. No. 506,865 filed Sept. 17, 1974 (now abandoned)
U.S. Ser. No. 615,093 Filed Sept. 19, 1975
U.S. Ser. No. 537,885 Filed Jan. 2, 1975 (now abandoned)
U.S. Ser. No. 618,023 Filed Sept. 30, 1975 (now abandoned)
U.S. Ser. No. 618,061 Filed Sept. 30, 1975 (now abandoned)
U.S. Ser. No. 618,021 Filed Sept. 30, 1975
U.S. Ser. No. 727,646 Filed Sept. 29, 1976 (now abandoned)
U.S. Ser. No. 782,986 Filed Mar. 30, 1977 (now U.S. Pat. No. 4,111,975, patented Sept. 5, 1978).

In the method of producing polyhydric alcohol(s) by the reaction of hydrogen and oxides of carbon in the presence of a rhodium carbonyl complex catalyst, the retention of the rhodium in solution is quite important since rhodium is an extremely expensive metal; it currently has a dealer's price of about $525 per troy ounce. Therefore, it is particularly desirable to minimize any loss of such rhodium values during the course of the reaction.

Also, in this process of producing polyhydric alcohol(s), glycerine is formed as a by-product. It has been determined that the build-up of glycerine causes a decrease in the rate of production of ethylene glycol and can also adversely affect the degree of retention of rhodium in solution.

It has been further discovered that under the reaction conditions of producing polyhydric alcohol(s) by the reaction of hydrogen and oxides of carbon in the presence of a rhodium carbonyl complex catalyst, there is a tendency for glycol to be destroyed. As a consequence, glycol is eventually produced at a decreased net rate and a relatively low upper limit is imposed on the concentration of glycol attainable in solution during the reaction.

In addition, when said reaction of producing polyhydric alcohol(s) is conducted in the presence of a salt promoter (as described in aforementioned patents and applications), the rate of reaction increases as a function of the stoichiometric concentration of salt promoter and then decreases.

It has now been found that when the production of polyhydric alcohol(s), by the reaction of hydrogen and oxides of carbon in the presence of a rhodium carbonyl complex catalyst, is conducted in the presence of a phosphine oxide compound(s) the following benefits are found: the rate of production of glycol can be increased; the degree of retention of rhodium in solution can be increased; the harmful effects of glycerine in the destruction of glycol are counteracted so that production of glycol is increased; and the use of excess salt promoters is permitted without effecting as large a decrease in the rate of formation of glycol.

In the evolution of the process for producing polyhydric alcohol(s) from hydrogen and oxides of carbon it was found that a desirable solvent in the homogeneous liquid phase system serves to separate ions without complexing the rhodium containing catalyst. In order to effect this result, the solvent should possess either a high dielectric constant or have the ability of complexing the available cations thereby freeing the available anions in the mixtures. For example, in U.S. Pat. Nos. 3,833,634 and 3,957,857, tetraglyme has been shown to be a particularly desirable solvent. It meets the above criteria because it is a good multidentate ligand for the available cations thereby reducing the interaction between the available cations and the available anions. Similarly, as shown in U.S. application Ser. No. 832,384, now U.S. Pat. No. 4,162,261 patented July 24, 1979, the crown ethers are very desirable solvents. On the other hand, as shown in U.S. application Ser. No. 615,093, now abandoned sulfolane meets the above criteria because it possesses a high dielectric constant which decreases the force of attraction between oppositely charged ions in the mixture. Butyrolactone, as covered in U.S. Pat. No. 3,986,136 functions in the same manner as sulfolane as a solvent in the aforementioned processes.

In U.S. application Ser. No. 618,021, there is disclosed the fact that when, e.g., sulfolane and tetraglyme, are employed in these processes as a solvent mixture there are obtained higher productivity and greater retention of the rhodium catalyst in the homogeneous liquid phase mixture. In order to obtain a beneficial effect from use of a solvent mixture, as compared to either pure component, the component's modes of action should be different. Use of a mixture could yield results which need not be intermediate of those obtained from use of either solvent because they could act synergistically, not merely complementarily, and the degree of harmful ion pairing could be less than in either solvent. For example, [18]-crown-6 is a good solvent at least in part because of its complexing ability; therefore, its best co-solvents should have high dielectric constants.

In the present invention the phosphine oxide can function as a solvent in the process of producing polyhydric alcohol(s) from hydrogen and oxides of carbon. Phosphine oxides are very strong Lewis bases toward the available cations and can therefore complex them. In this sense, they meet the above criteria in the way that tetraglyme and crown ethers do. In addition they possess dieletric constants significantly higher than those of tetraglyme and the crown ethers. In that sense, they meet the criteria also in the way that sulfolane and butyrolactone do. Previously, the desirable solvents met the above criteria in one way or another, but not in both ways. Tetraglyme and the crown ethers are good multidentate ligands for the available cations, but have relatively low dielectric constants; sulfolane and butyrolactone possess high dielectric constants, but are relatively poor at complexing the available cations. Phosphine oxides can meet the above criteria to a significant extent in both ways because they possess substantial dielectric constants and also can form strong complexes with the available cations.

Salts containing alkali metal cations have been utilized to improve the yield of alkane polyols produced from hydrogen and oxides of carbon. In U.S. Pat. No. 3,952,039, a metal salt is provided to the aforementioned homogeneous liquid phase reaction mixture to promote the production of alkane polyols, ethylene glycol being the primary product in terms of its commercial value. The salt promoter provided to the mixture is present in an amount to achieve the optimum rate of formation of said alkane polyol at the correlated catalyst concentration, temperature and pressure of such reaction mixture. A range of 0.5–1.5 atoms of cation per six atoms of rhodium is disclosed in the patent. When the amount of alkali metal cation in the reaction is greater or less than this amount, the productivity of reaction to polyhydric alcohol is significantly reduced.

In U.S. patent application Ser. No. 800,897 filed May 26, 1977 (now abandoned) the possible mechanics which could result in the above-described behavior were postulated as follows:

(a) the inhibitor function of the salt is of higher kinetic order in salt than is the promoter function;
(b) the promoter function of the salt has a stoichiometric limit after which only the inhibitor function of the salt remains.

The term "inhibitor function" means the function of the salt which results in a decrease in alkane polyol rate of formation as salt concentration increases.

An above postulate can be illustrated by the following reaction scheme:

The involvement of salt is described as follows:
(Rh symbolizes a rhodium-containing species):

[NOTE: In the above reaction scheme the charge of the rhodium carbonyl complex is not shown; it contains a fixed or varying number of CO's and H's; the rate and equilibrium constants implicity contain any appropriate CO and $H_2$ concentrations.] The salt acts as a promoter because its anion helps to produce the active catalyst and as an inhibitor because its cation has an adverse mass law effect on the equilibrium concentration of a direct precursor of the active catalyst. The model suggests the use of a salt and reaction conditions which produce a reactive anion and an impotent cation.

The model predicts that the rate will increase as a function of the stoichiometric concentration of salt promoter, and then decrease. As K increases, either because of an intrinsic property of $M^+$ or use of a solvent of high dielectric constant (for example, sulfolane) or high constant of complexation with $M^+$ (for example, crown ether, and to a lesser extent tetraglyme), the rate of decrease decreases. Any complexation of the cation by the solvent is incorporated implicitly into the definition of K as a result of the customary definition of standard states.

Thus, the process of U.S. Pat. No. 3,952,039 recognizes that there is an optimum concentration for salt promoters to achieve maximum alkane polyol production and that amounts in excess of that optimum concentration are undesirable. The process of Serial No. 800,897 contemplates increasing the concentration of the salt in excess of said optimum concentration for the purpose of enhancing catalyst stability in the reaction. Also, it was recognized in Ser. No. 800,897 that allowing for some excess of the salt over the optimum concentration will reduce the criticality of having to operate the process under strict control of salt concentration.

Figure 1:
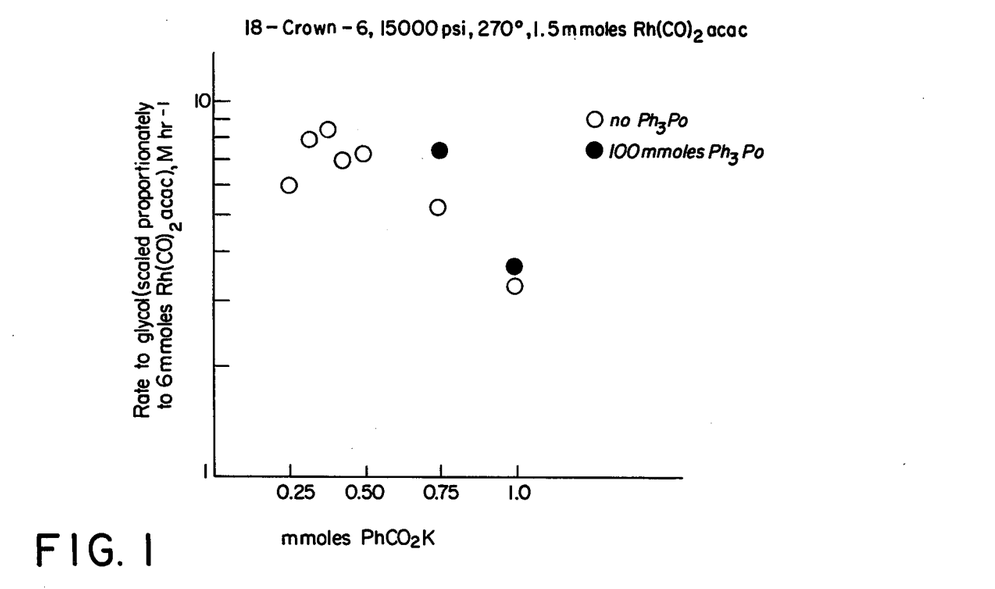
Figure 2:
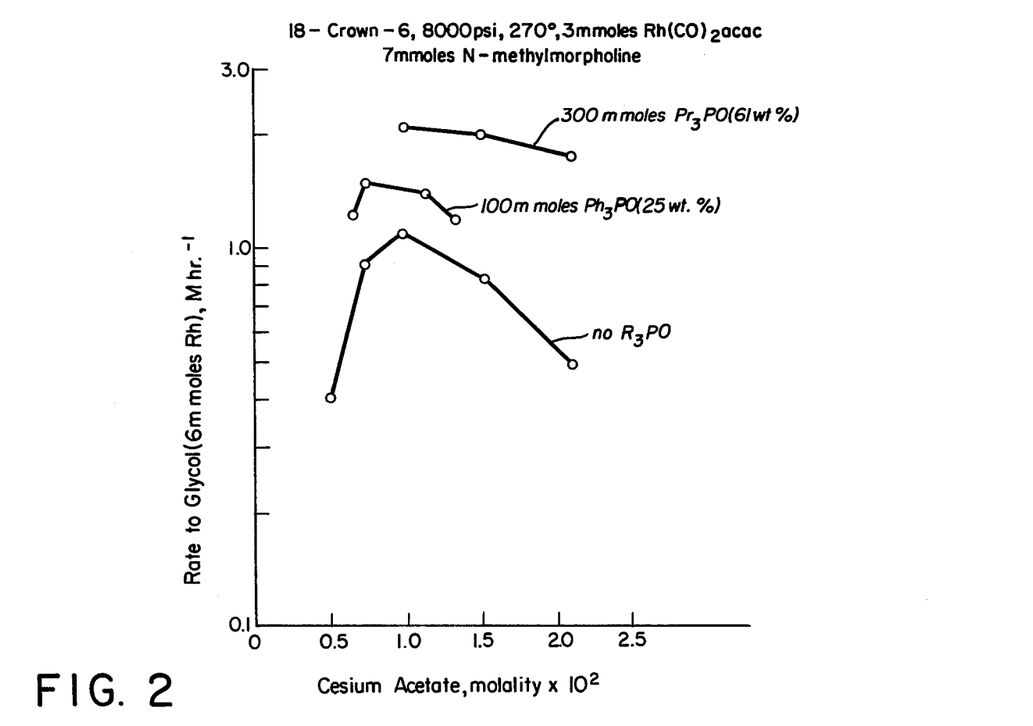

The process of the present invention employs phosphine oxide which may shift the equilibrium of equation (1) to the right. As discussed above, this may result from its properties as a (co)-solvent. Also, since phosphine oxides are very strong Lewis bases toward the $M^+$ of equation (1), they may function as a promoter and they may decrease the ion-pairing ability of $M^+$ by complexing with it. The result of its promoter/solvent function is an increase in the rate of reaction and the ability to use excess salt promoter without as large a decrease in the rate of formation of alkane polyol as occurred previously in the absence of phosphine oxides. (See FIGS. 1 and 2). Also, phosphine oxides provide good retention of the rhodium catalyst in solution under the conditions which provide such higher rates of formation of alkane polyol(s).

Phosphine oxides are known to be very strong hydrogen bond acceptors. Thus, phosphine oxide could serve to complex with glycol and glycerine, both of which are bifunctionally chelating hydrogen bond donors, to stabilize them against subsequent reaction which causes inhibition and loss of glycol. As a consequence, the harmful effects of glycerine and of glycol as described above can be counteracted.

The process of this invention involves, as stated above, the manufacture of alkane polyols. This includes the reaction of a mixture of hydrogen and oxides of carbon in a homogeneous liquid phase mixture containing a catalytic amount of rhodium carbonyl complex and a phosphine oxide compound(s). The reaction is carried out at a temperature of between about 100° C. and about 450° C. and at a pressure between about 500 psia and 50,000 psia sufficient to produce the alkane polyol.

The phosphine oxide compounds suitable for the practice of the process of the present invention are those which include a single phosphoryl group, and the remaining atoms bonded to the phosphorus are carbon which may be substituted by at least another carbon atom, hydrogen, fluorine and/or oxygen. The phosphine oxide compounds should be free of sulfur atoms and halogen atoms except fluorine.

Illustrative of the phosphine oxide compounds which are suitable in the practice of this invention are those which are characterized by the following formulae:

I.

wherein $R_1$, $R_2$ and $R_3$ are independently:

(1) straight or branched chain alkyl having 1 to 20 carbon atoms, preferably having 1 to 12 carbon atoms, most preferably 1 to 6 carbon atoms, such as methyl, ethyl, isopropyl, butyl, octyl, dodecyl, octadecyl and the like;

(2) substituted alkyl wherein the substituents may be:
(a) fluorine, such as in $CF_3$,
(b) those of the formula $(-O-R°)$ wherein R° may be hydrogen, aryl or lower alkyl having from 1 to 12 carbon atoms, preferably 1 to 4 carbon atoms,
(c) those of the formulae $(-OC_nH_{2n})_x$ OR° or $(-OCHCH_3C_aH_{2a})_x$ OR° wherein n has an average value of from 2 to about 4, x has an average value of from 1 to about 1000 and R° is as previously defined;

(3) a group of the formulae:

wherein y may have any value between 1 and 12, m and m° may be zero or one provided that when either m or m° is one the other is zero; $R_4$ is an alkylene or oxyalkylene radical having 1 to 12 carbon atoms or an arylene radical, $R_5$ is an alkyl radical having from 1 to 12 carbon atoms, preferably from 1 to 4 carbon atoms, or aryl;

(4) a cycloaliphatic group including the monocyclic and bicyclic groups such as cyclopropyl, cyclopentyl, cyclohexyl, bicyclo[2.2.1]heptyl, and the like;

(5) an aryl, alkylaryl, or aralkyl group which may be substituted by $R_1$ or by substituents (a) to (c);

II. Heterocycloalkylene such as:

wherein $R_7$ is an alkylene radical of 3 to 20 carbon atoms or -O-alkylene- wherein the alkylene contains 3 to 20 carbon atoms which alkylene radicals may be substituted by $R_1$, wherein $R_1$ is as previously defined, or by an oxo group, or by substituents (a) to (c).

III.

wherein $R_1$ is as previously defined or one of substituents (a) to (c) and x is 0 to 4.

Phosphine oxides within the scope of formulas I through III are as follows:

$$\overset{O}{\underset{}{\overset{\parallel}{P}}}(CF_3)_3 \quad \overset{O}{\underset{}{\overset{\parallel}{P}}}(F_5C_6)_3$$

$$\overset{O}{\underset{}{\overset{\parallel}{P}}}(CH_3)_3 \quad \overset{O}{\underset{}{\overset{\parallel}{P}}}(C_6H_4F)_3$$

$$\overset{O}{\underset{}{\overset{\parallel}{P}}}(CH_2OH)_3 \quad \overset{O}{\underset{}{\overset{\parallel}{P}}}(C_6H_{13})_3$$

$$\overset{O}{\underset{}{\overset{\parallel}{P}}}(CH_2CO_2CH_3)_3 \quad \overset{O}{\underset{}{\overset{\parallel}{P}}}(CH_2C_6H_5)_3$$

$$\overset{O}{\underset{}{\overset{\parallel}{P}}}(CH_2O_2CCH_3)_3$$

$$\overset{O}{\underset{}{\overset{\parallel}{P}}}(C_3H_7)_3$$

$$\overset{O}{\underset{}{\overset{\parallel}{P}}}(CH_2CH_2CO_2C_2H_5)_3 \quad \overset{O}{\underset{}{\overset{\parallel}{P}}}(C_7H_{15})_3$$

$$\overset{O}{\underset{}{\overset{\parallel}{P}}}(C_6H_5)_3$$

(CH₂OCH₂CH₂OCH₃)₂
(CH₃O₂CC₆H₄)₃PO
[C₆H₅CH(OCH₃)]₃PO (9-Phenanthryl)₃PO

These phosphine oxides are known in the art and are prepared according to methods as set forth in, for example, G. M. Kosolapoff et al "Organic Phosphorus Compounds", Volume 3, John Wiley & Sons, Inc., 1972, pp 341–500, which is incorporated herein by reference.

The preferred phosphine oxides include

The phosphine oxide are used in amounts of 0.01 to 100 weight percent of the mixture exclusive of products, preferably 0.1 to 100 weight percent.

The rhodium carbonyl complex catalysts may be in the form of rhodium carbonyl clusters or derived from a cluster form. P. Chini, in a review article entitled "The Closed Metal Carbonyl Clusters" published in Review (1968), Inorganica Chimica Acta, pages 30–50, states that a metal cluster compound is "a finite group of metal atoms which are held together entirely, mainly, or at least to a significant extent by bonds directly between the metal atoms even though some non-metal atoms may be associated intimately with the cluster". The rhodium carbonyl clusters contain rhodium bonded to rhodium or rhodium bonded to another metal, such as cobalt and/or iridium. The preferred rhodium carbonyl cluster compounds are those which contain rhodium-rhodium bonds. These compounds desirably contain carbon and oxygen in the form of carbonyl (—CO), in which the carbonyl may be "terminal", "edge-bridging", and/or "face-bridging". They may also contain hydrogen and carbon in forms other than carbonyl. The structure of two distinct rhodium carbonyl clusters having the respective empirical formulas, $Rh_6(CO)_{16}$ and $Rh_{12}(CO)_{30}{}^{2-}$, and which are suitable for use in this invention, are shown for example in U.S. Pat. No. 3,957,857.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chimica Acta, 3:2 pp 299–302, June (1969).

A number of nitrogen and/or oxygen-containing bases may be used in the process of the present invention. For the purposes of this invention, the bases can be considered to promote the activity of the rhodium catalysts.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino(—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), all of said groups containing Lewis base oxygen atoms. In this respect, it is the "hydroxyl" oxygen in the $$\underset{\text{—COH}}{\overset{\text{O}}{\|}} \text{ group}$$

and the "oxy" oxygen in the $$\underset{\text{—CO—}}{\overset{\text{O}}{\|}} \text{group}$$

that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid, ethylenediaminetetraacetic acid; 2,6-dicarboxypyridine;

8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di-, tri-, tetraamines, etc.) and those compounds in which the Lewis base nitrogen forms part of a ring structure as in pyridine, quinoline, pyrimidine, morpholine, hexamethylenetetraamine, and the like. In addition any compounds capable of yielding an amino nitrogen under the reaction conditions of the present invention are promoters, as in the case of an amide, such as formamide, cyanamide, and urea, or an oxime. Further illustrative of Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino) pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'-dipyridyl, methyl-substituted 2,2'-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo[2.2.2]octane, purine and the like.

Also included herein are the use of dimorpholine compounds characterized by the formula:

wherein R is divalent alkylene of 1 to about 30 carbon atoms and 1,4-phenylene.

The base provided to the reaction mixture is present in an amount which is equal to or greater than that amount, determined from the bases basicity, which achieves the optimum rate of formation of said alkane polyol at said correlated catalyst concentration, temperature and pressure of such reaction mixture.

The concentration of the base will typically be within about 0.001 to about 10 molar. Obviously this range is definitive of the potential scatter of concentrations predicated on the varieties of the basicities of the bases available.

Under reaction conditions the base is preferably used in amounts from about 0.02 to about 40 equivalents of base, most preferably from about 0.1 to about 20 equivalents base, for every atom of rhodium in the reaction mixture. The number of equivalents of base is equal to the number of molecules of base times the number of nitrogen atoms in each molecule.

In practicing the method of the present invention, the synthesis of the desired alkane diols and derivatives thereof, by the reaction of hydrogen with an oxide of carbon is suitably conducted under operative conditions, as heretofore described, which give reasonable reaction rates and/or conversions.

The process is suitably effected over a wide superatmospheric pressure range of from about 800 psia to about 50,000 psia. Pressures as high as 50,000 psia, and higher can be employed but with no apparent advantages attendant thereto which offset the unattractive plant investment outlay required for such high pressure equipment. Therefore, the upper pressure limitation is desirably approximately 16,000 psia. Effecting the present process below about 16,000 psia, especially below about 13,000 psia, and preferably at pressures below about 8000 psia, results in cost advantages which are associated with low pressure equipment requirements. In attempting to foresee a commercial operation of this process, pressures between about 4,000 psia and 16,000 psia appear to represent most realistic values.

In a preferred embodiment of the present invention the pressures referred to above represent the total pressures of hydrogen and oxides of carbon in the reactor.

The process of this invention can also be carried out by providing salts in the homogeneous liquid phase reaction mixture. Suitable salts include any organic or inorganic salt which does not adversely affect the production of polyhydric alcohols. Experimental work suggest that any salt is beneficial as either a copromoter and/or in aiding in maintaining rhodium in solution during the reaction. Illustrative of the salts useful in the practice of the present invention are the ammonium salts and the salts of the metals of Group I and Group II of the Periodic Table (Handbook of Chemistry and Physics-50th Edition) for instance the halide, hydroxide, alkoxide, phenoxide and carboxylate salts such as sodium fluoride, cesium fluoride, cesium pyridinolate, cesium formate, cesium acetate, cesium benzoate, cesium p-methylsulfonylbenzoate (CH$_3$SO$_2$C$_6$H$_4$COO)Cs, rubidium acetate, magnesium acetate, strontium acetate, ammonium formate, ammonium benzoate and the like. Preferred are the cesium, rubidium, potassium, and ammonium salts.

Also useful in the practice of the present invention are organic salts of the following formula:

quaternary ammonium salts bis(triorgano phosphine)iminium salts wherein $R_1$ through $R_6$ in formulas (I) and (II) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups, cyclopentyl, cyclohexyl, and bicyclo[2.2.1]heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $(C_nH_{2n}O)_x$-OR wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas I and II above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas I and II, above, is a carboxylate, most preferably formate, acetate and benzoate.

A suitable method for preparing the bis(triorganophosphine) iminium salts is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In addition, the anion of the above salt may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; $[Rh_{12}(CO)_{30}]^{2-}$; $Rh_{13}(CO)_{24}H_3^{-2}$; and $Rh_{13}(CO)_{24}H_2^{-3}$.

Under reaction conditions where a salt is employed, the salt is desirably added with the initial charge of reactants in amounts of from about 0.5 to about 2.0 molecules, preferably from about 0.8 to about 1.6 molecules, and most preferably from about 0.9 to 1.4 molecules of salt for every five atoms of rhodium present in the reaction mixture.

Illustrative solvents which are generally suitable in making the homogeneous mixture include, for example, ethers such as tetrahydrofuran, tetrahydropyran, diethyl ether, 1,2-dimethoxybenzene, 1,2-diethoxybenzene, the mono- and dialkyl ethers of ethylene glycol, of propylene glycol, of butylene glycol, of diethylene glycol, of butylene glycol, of diethylene glycol, of dipropylene glycol, of triethylene glycol, of tetraethylene glycol, of dibutylene glycol, of oxyethylenepropylene glycol, etc; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate etc.; water; gamma-butyrolactone, deltavalerolactone; substituted and unsubstituted tetrahydrothiophene-1,1-dioxides (sulfolanes) as disclosed in U.S. application Ser. No. 537,885, filed on Jan. 2, 1975. These include sulfolanes of the formula:

wherein each of $R_1$ through $R_8$ is at least one of hydrogen; hydroxyl; straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo[2.2.1]heptyl, and the like; or an aryl, alkyl-aryl, or aralkyl group such as phenyl, naphthyl, xylyl, tolyl, benzyl, beta-phenylethyl and the like; an ether of the formula $+O-R°$ wherein R° may be aryl or lower alkyl having from 1 to 12 carbon atoms, preferably 1 to 4 carbon atoms in the alkyl chain; an alkylene or polyalkylene ether of the formula $-(OC_nH_{2n})_x+OR°°$ wherein n has an average value of from 1 to about 4, x has an average value of from 1 to about 150, preferably 1 to about 20, most preferably 1 to about 4, and R°° may be hydrogen or alkyl having from 1 to 6 carbon atoms in the alkyl chain, such as poly(oxyethylene), poly(oxyethylene-oxypropylene), alkylene and polyalkylene glycols and lower alkyl ethers thereof; a carboxylate group of the formula:

wherein y may have value between 0 and 12, m and m° may be zero or one provided that when either m or m° is one the other is zero, and R°°° may be a lower alkyl group having from 1 to 12 carbon atoms, preferably from 1 to 4 carbon atoms, or aryl, and the like.

Also, the crown ethers are suitable herein, particularly those as described in U.S. patent application Ser. No. 832,384 filed Sept. 13, 1977, which is incorporated by reference herein and is now U.S. Pat. No. 4,162,261.

The crown ethers contain in the principal ring at least 4 oxygen atoms each separated from the other by at least two aliphatic carbon atoms in series. The principal ring contains at least two ring oxygen atoms which are each joined to ethylene or substituted ethylene groups. The remainder of the principal ring oxygen atoms are joined to either trimethylene, tetramethylene, substituted trimethylene, or substituted tetramethylene groups, or mixtures of them. The maximum number of ring oxygen atoms in the principal ring may be as much as about 100, however, it is desirable that those ring oxygen atoms joined to groups other than ethylene or substituted ethylene number not more than about 50 when the number of such ring oxygen atoms exceeds about 52.

These crown ethers include [18]-crown-6 and [15]-crown-5.

The preferred solvents for practising the invention are a number of solvents which have heretofore been described in the production of alkane polyols from synthesis gas.

Particularly desirable solvents are tetraglyme, sulfolane, gamma-butyrolactone and the crown ethers. Other very desirable solvents include mixtures of tetraglyme and sulfolane, mixtures of sulfolane and butyrolactone, mixtures of crown ethers and sulfolane, mixtures of crown ethers and tetraglyme, mixtures of crown ethers and butyrolactone, and mixtures of tetraglyme and butyrolactone.

The temperature which may be employed can vary over a wide range of elevated temperatures. In general, the process can be conducted at a temperature in the range of from about 100° C. and upwards to approximately 375° C., and higher. Temperatures outside this stated range are not excluded from the scope of the invention. At the lower end of the temperature range, and lower, the rate of reaction to desired product becomes markedly slow. At the upper temperature range, and beyond, signs of some catalyst instability are noted. Notwithstanding this factor, reaction continues and alkane polyols and/or their derivatives are produced. Additionally, one should take notice of the equilibrium reaction for forming ethylene glycol

2 CO+3H$_2$⇌HOCH$_2$CH$_2$OH

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher pressures, however, do not represent preferred embodiments of the invention in view of the high investment costs associated with erecting chemical plants which utilize high pressure utilities and the necessity of fabricating equipment capable of withstanding such enormous pressures. However, such high pressures may prove to be justified economically because of high rates of glycol production and enhanced retention of rhodium in solution. Suitable temperatures are between about 150° C. to about 350° C., and desirably from about 210° C. to about 320° C.

The process is effected for a period of time sufficient to produce the alkane polyols and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressures exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of CO:H$_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by virbration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction.

Means to introduce and/or adjust the reactants, either intermittently or continuously, into the reaction zone during the course of the reaction can be conveniently utilized in the novel process especially to maintain the desired molar ratios of and the partial pressures exerted by the reactants.

The operative conditions can be adjusted to optimize the conversion of the desired product and/or the economics of the process. In a continuous process, for instance, when it is preferred to operate at relatively low conversions, it is generally desirable to recirculate unreacted synthesis gas with/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and intermittently added to the recycle stream or directly to the reaction zone.

The active forms of the rhodium carbonyl complex may be prepared by various techniques. They can be preformed and then introduced into the reaction zone or they can be formed in situ.

In situ catalyst formation will, in all probability, constitute the preferred method, if not the only method.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Pat. No. 3,957,857 the disclosure of which is incorporated herein by reference.

A particularly desirable infrared cell construction is described in U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction.

The following examples are merely illustrative and are not presented as a definition of the limits of the invention:

Triphenylphosphine oxide (Aldrich Chemical Co.) and tributylphosphine oxide (Eastman Chemical Co.) were recrystallized from ethanol and benzene, respectively, and were shown by use of Vpc analysis to contain less than 0.03% of the corresponding phosphine.

$(CH_3OCH_2CH_2OCH_2)_2P(O)CH_3$ was prepared by the procedure of E. N. Tsvetkov, G. Borisov, Kh. L. Sivriev, R. A. Malevannaya and M. I. Kabachnik, Zh. Obshch. Khim., 40, 285(1970) and the reaction sequences are as follows:

It was purified by use of fractional distillation bp 153°/1.5 mm; nmr (DMSO): $\tau=6.18$(d,J=6 cps, 4H), 6.2–6.6(m, 8H), 6.71(s, 6H), 8.61(d, J=13 cps, 3H).

Tripropylphosphine oxide (Orgmet Chemical Co.) was purified by distillation, bp 106°–7°/3 mm. Mp 41.5°–42.5°. Nmr (CDCl$_3$): $\tau=8.0$–8.8 (m, 12H), 8.8–9.2(m, 9.0H); the spectrum showed no extraneous absorption when recorded with the $\tau=8.0$–9.2 peaks 10 times full scale.

The trimethylphosphine oxide (Orgmet Chemical Co.) used was purified by sublimation [J. Gourbeau and W. Berger, Z. Anorg. Allgem. Chem., 304, 147(1960); M. D. Joesten and R. S. Drago, J. Am. Chem. Soc., 84, 3817(1962)] at 70°/1 mm. Mp 140°–3°. Nmr(CDCl$_3$); $\tau=8.42$ (d,J=13.5 cps); the spectrum showed no extraneous absorption when recorded with the $\tau=8.42$ peaks 10 times full scale.

Procedure

A 150 ml. capacity stainless steel reactor capable of withstanding pressures up to 7,000 atmospheres was charged with a premix of 75 cubic centimeters (cc) of the indicated solvent(s), the indicated amount (mmoles) of phosphine oxide, 3.0 millimoles (mmol) of rhodium dicarbonylacetylacetonate, salt and amine. The reactor was sealed and charged with a gaseous mixture, containing equal molar amounts of carbon monoxide and hydrogen to a pressure of 8,000 pounds per square inch (psig). Heat was applied to the reactor and its contents; when the temperature of the mixture inside the reactor reached 220° C., as measured by a suitably placed thermocouple, an additional adjustment of carbon monoxide and hydrogen (H$_2$:CO=1:1 mole ratio) was made to bring the pressure back to 8000 psig. The temperature (in °C.) as set forth in Table I, was maintained at the desired value for 4 hours. During this period of time additional carbon monoxide and hydrogen was added whenever the pressure inside dropped below about 7500 psig. With these added repressurizations the pressure inside the reactor was maintained at 8000 psig ±400 psig over the entire 4 hour period.

After the 4 hour period, the vessel and its contents were cooled to room temperature, the excess gas vented and the reaction product mixture was removed. Analysis of the reaction product mixture was made by gas chromatographic analysis using a Hewlett Packard FM TM model 810 Research Chromatograph.

Rhodium recovery was determined by atomic absorption analysis of the contents of the reactor after the venting of the unreacted gas at the end of the reaction. The rhodium recovery values recited below are the percent rhodium based on the total rhodium charged to the reactor that is soluble or suspended in the reaction mixture after the specified reaction time.

EXAMPLES 1 TO 16

The Procedure is followed and additionally, an amount (g) of ethylene glycol is added initially. The results are set forth in Table I.

Examples 2 compared with 3 and 4; 6 compared with 7; 9 compared with 10; 12 compared with 14 and 16; and 13 compared with 15 show that rhodium recovery is enhanced and that less glycol is destroyed, which results in increased glycol production, when a phosphine oxide is present.

TABLE I
Effect of Phosphine Oxides on Degree of Destruction of Glycol and Retention of Rhodium in Solution

| Ex. | Phosphine Oxide (mmoles)[1] | Glycol Added Initially, (g) | Salt (mmoles)[2] | Amine (mmoles) | Solvent | Temp. (°C.) | Wt. of Product Methanol, (g) | Wt. of Product Ethylene glycol, (g) | % Rh Rec'd | Ethylene-Glycol Destroyed[d] (g) |
|---|---|---|---|---|---|---|---|---|---|---|
| 1 | — | — | HCO$_2$Cs(0.65) | Triisopropanolamine borate (2.5) | Sulfolene | 240 | 4.37 | 6.09 | 84 | — |
| 2 | — | 6.0 | " | " | " | " | 4.89,4.62 | 9.84,9.90 | 90,88 | 1.88,1.81 |
| 3 | Ph$_3$PO(50) | 6.0 | " | " | " | " | 4.57 | 10.08 | 94 | 1.61 |
| 4 | Ph$_3$PO(100) | 6.0 | " | " | " | " | 4.52 | 10.91 | 99 | 0.70 |
| 5 | — | — | PhCO$_2$Cs(0.65) | N-methylmorpholine(5.0) | " | 250 | 5.47 | 6.40 | 76 | — |
| 6 | — | 6.0 | " | " | " | " | 4.95 | 10.88 | 73 | 1.07 |
| 7 | Ph$_3$PO(100) | 6.0 | " | " | " | " | 4.05 | 11.70 | 78 | 0.17 |
| 8 | — | — | HCO$_2$Cs(0.65) | Pyridine(1.25) | Tetraglyme | 240 | 4.46 | 5.97 | 60 | — |
| 9 | — | 6.0 | " | " | " | " | 4.56 | 10.36 | 62 | 1.17 |
| 10 | Ph$_3$PO(100) | 6.0 | " | " | " | " | 6.55 | 11.34 | 81 | 0.10 |
| 11 | — | — | PhCO$_2$Cs(0.62)[a] | N-methylmorpholine(2.5) | " | 240 | 3.68,[b]1.86,[c]6.96 | 7.29,[b]7.43,[c]6.70 | 96,77,102 | — |
| 12 | — | 4.0 | " | " | " | " | 6.54 | 9.70 | 79 | 1.18 |
| 13 | — | 7.5 | " | " | " | " | 5.12 | 11.28 | 82 | 2.94 |
| 14 | Ph$_3$PO(100) | 4.0 | " | " | " | " | 3.00 | 13.04 | 87 | −2.49 |
| 15 | Ph$_3$PO(125) | 7.5 | " | " | " | " | 2.96 | 15.71 | 93 | −1.93 |
| 16 | Bu$_3$PO(100) | 4.0 | " | " | " | " | 2.57 | 13.35 | 95 | −2.84 |

[a]Reaction run at 15,000 psi and 50 min.
[b]Scaled proportionately from 0.75 to 0.83 hr.
[c]Scaled proportionately from 1.16 to 0.83 hr.
[d](glycol produced in a run containing no glycol initially) - ("additional" glycol produced in a run containing glycol initially). Corrected approximately for non-quantitative recovery of reaction mixture from reactor.
[1]Ph$_3$PO - triphenylphosphine oxide
Bu$_3$PO - tributylphosphine oxide
[2]HCO$_2$Cs - cesium formate
PhCO$_2$Cs - cesium benzoate

EXAMPLES 17 TO 26

The Procedure was exactly repeated except that in Examples 17 to 21 the pressure was 15000 psia and reaction time was 50 minutes. In Examples 22 to 26 pressure was 12,500 psia and reaction time was 46 minutes. Also, in Examples 18 to 21 and 23 to 26, glycerine, in the amount as set forth in Table II, was added to the reaction. The data of Table II show that glycerine reduces both the amount of ethylene glycol produced as well as decreasing the amount of rhodium recovered from solution. When phosphine oxide is added to the reaction it counteracts the effect of glycerine on ethylene glycol production and rhodium recovery.

EXAMPLES 27 TO 31

The Procedure was exactly repeated except that the reaction pressure was 15,000 psi. Also, in Examples 28 and 29 ethylene glycol was added to the reaction while in Examples 30 and 31 glycerine was added to the reaction. The data in Table III shows that phosphine oxide counters the harmful effects of ethylene glycol and glycerine on ethylene glycol production in 18-crown-6 solvent.

TABLE III

Phosphine Oxide Effect on Glycol and Glycerine Effects

| Ex. | Ethylene Glycol Initially Added, (g) | Glycerine Added Initially, (g) | Phosphine Oxide,[a] (g) | Salt (mmoles) | Amine (mmoles) | Solvent | Temp. (°C.) | Rate,[b] Mhr$^{-1}$ Methanol | Ethylene Glycol | % Rh Recovered |
|---|---|---|---|---|---|---|---|---|---|---|
| 27 | — | — | — | KHCO$_3$(0.78) | N-methyl-morpholine(6) | 18-crown-6 | 250 | 0.75,1.12 | 2.77,2.77 | 89,93 |
| 28 | 3.0 | — | — | " | N-methyl-morpholine(6) | " | " | 1.8 | 2.18 | 92 |
| 29 | 3.0 | — | Bu$_3$PO (10.9)[1] | " | N-methyl-morpholine(6) | " | " | ~1.1 | 3.31 | 96 |
| 30 | — | 3.0 | — | " | N-methyl-morpholine(6) | " | " | 1.9 | 2.2 | 81 |
| 31 | — | 3.0 | Bu$_3$PO(7.8) | " | N-methyl-morpholine(6) | " | " | ~1.3 | 2.87 | 87 |

[a]Amount of phosphine oxide added corresponds to an equimolar amount based on the ethylene glycol and glycerine added.
[b]Based on 75 ml of solvent.
[1]Bu$_3$PO - Tributylphosphine oxide

EXAMPLES 32 TO 42

The Procedure was exactly repeated except that the pressure and amount of rhodium dicarbonylacetylacetonate were as indicated and the reaction time was not 4 hrs. The data in Table IV show that the addition of phosphine oxide to the reaction increased the amount of rhodium retained in solution.

TABLE II

Ph$_3$PO Counteracts Effect of Glycerine on Rate

| Ex. | Glycerine Added Initially, (g) | Salt(mmoles)[1] | Amine(mmoles) | Solvent | Temp. (°C.) | Phosphine Oxide (mmoles)[a] | Ethylene Glycol, (g) | % Rh Recovered |
|---|---|---|---|---|---|---|---|---|
| 17 | — | PhCO$_2$Cs(0.615) | N-methylmorpholine(2.5) | Tetraglyme | 240 | — | 7.29,[b]7.43,[c]6.70 | 96,77,102 |
| 18 | 5.0 | " | " | " | " | — | 6.38 | 93 |
| 19 | 5.0 | " | " | " | " | Ph$_3$PO(60)[2] | 8.10 | 104 |
| 20 | 15.0 | " | " | " | " | — | 2.81 | 85 |
| 21 | 15.0 | " | " | " | " | Ph$_3$PO(180) | 7.58 | 88 |
| 22 | — | PhCO$_2$Cs(0.615) | Pyridine(1.25) | Tetraglyme/Sulfolane 38/38(v/v) | 260 | — | 10.48,10.93 | 98,106 |
| 23 | 5.0 | " | " | Tetraglyme/Sulfolane 38/38(v/v) | " | — | 9.13 | 103 |
| 24 | 5.0 | " | " | Tetraglyme/Sulfolane 38/38(v/v) | " | Ph$_3$PO(60) | 8.71 | 99 |
| 25 | 15.0 | " | " | Tetraglyme/Sulfolane 38/38(v/v) | " | — | 4.97 | 92 |
| 26 | 15.0 | " | " | Tetraglyme/Sulfolane 38/38(v/v) | " | Ph$_3$PO(180) | 7.76 | 101 |

[a]5g of glycerine requires 60 mmoles Ph$_3$PO to give an equimolar amt. of Ph$_3$PO
[b]Scaled from 0.75 to 0.83 hr.
[c]Scaled from 1.16 to 0.83 hr.
[1]PhCO$_2$Cs - cesium benzoate
[2]Ph$_3$PO - triphenylphosphine oxide TABLE IV[b]

| Ex. | Phosphine Oxide (mmoles)[1] | Salt(mmoles)[2] | Amine (mmoles) | 18-crown-6 ml | Temp (°C.) | Pressure (psi) | Rate,[a] Mhr$^{-1}$ Methanol | Ethylene glycol | % Rh Recovered |
|---|---|---|---|---|---|---|---|---|---|
| 32 | — | PhCO$_2$Cs(0.375) | N-methylmorpholine(7) | 75 | 280 | 15,000 | 12 | 14 | 61 |
| 33 | Ph$_3$PO(100) | " | " | " | " | " | 9.6 | 15 | 82 |
| 34 | — | PhCO$_2$Cs(0.425) | " | " | " | " | 12,13 | 12,13 | 49,68 |
| 35 | Ph$_3$PO(100) | " | " | " | " | " | 9.1 | 14 | 82 |
| 36 | — | PhCO$_2$K(0.425) | N-methylmorpholine(4) | " | " | " | ~11 | 15 | 63 |
| 37 | Ph$_3$PO(100) | " | " | " | " | " | 8.6 | 12 | 86 |
| 38 | — | PhCO$_2$K(0.50) | N-methylmorpholine(7) | " | " | " | ~9 | 9.8 | 56 |
| 39 | Ph$_3$PO(100) | " | " | " | " | " | 9.2 | 13 | 81 |
| 40 | Pr$_3$PO(200) | " | " | 45 | " | " | 7 | 13 | 78 |
| 41 | Pr$_3$PO(370) | " | " | — | " | " | 8,12 | 13,18 | 107,90 |
| 42 | Me$_3$PO(150) | " | " | 75 | " | " | 8.7 | 13 | 82 |

[a]Scaled proportionately to 6 mmoles of rhodium dicarbonylacetylacetonate. Based on 75 ml of solvent.
[b]1.5 mmoles of rhodium dicarbonylacetylacetonate.
[1]Ph$_3$PO - triphenylphosphine oxide.
Pr$_3$PO - tripropylphosphine oxide.
Me$_3$PO - trimethylphosphine oxide
[2]PhCO$_2$Cs - cesium benzoate.
PhCO$_2$K - potassium benzoate.

EXAMPLES 43 TO 65

TABLE V

| Ex. | Phosphine Oxide[2] (mmoles) | Salt (mmoles)[1] | Amine (mmoles) | Temp.(°C.) | Pressure (psi) | Rate,[a] Mhr$^{-1}$ Methanol | Ethylene Glycol | % Rh Recovered |
|---|---|---|---|---|---|---|---|---|
| 43 | — | CsOAc (0.85) | N-methylmorpholine(7) | 270 | 8000 | ~1.7,1.7 | 1.12,1.16 | 56,51 |
| 44 | — | PhCO$_2$Cs(0.85) | " | " | " | 1.9 | 1.06 | 59 |
| 45 | Ph$_3$PO(100) | CsOAc (0.75) | " | " | " | 1.5 | 1.21 | 58 |
| 46 | " | CsOAc (0.85) | " | " | " | 1.7,1.7 | 1.53,1.44 | 65,62 |
| 47 | " | CsOAc (1.3) | " | " | " | 1.9 | 1.39 | 64 |
| 48 | " | CsOAc (1.5) | " | " | " | 2.2 | 1.19 | 76 |
| 49 | " | CsOAc (0.85) | N-methylmorpholine(2) | " | " | 1.4 | 1.27 | 73 |
| 50 | " | " | N-methylmorpholine(4) | " | " | 1.8 | 1.33 | 70 |
| 51 | " | " | N-methylmorpholine(7) | " | " | 1.7,1.7 | 1.53,1.44 | 65,62 |
| 52 | " | " | N-methylmorpholine(14) | " | " | 1.4 | 1.35 | 55 |
| 53 | Bu$_3$PO(100) | " | N-methylmorpholine(7) | " | " | ~1.0 | 1.35 | 55 |
| 54 | Ph$_3$PO(100) | PhCO$_2$Cs(0.85) | " | " | " | 1.5 | 1.32 | 62 |
| 55 | Ph$_3$PO(100) | Me$_2$CHCO$_2$Cs(0.85) | " | " | " | 1.8 | 1.47 | 56 |
| 56 | Ph$_3$PO(100) | CsOAc (1.3) | ethylenedimorpholine(7) | " | " | 1.9 | 1.24 | 62 |
| 57 | Ph$_3$PO(10) | CsOAc (0.85) | N-methylmorpholine(7) | " | " | 1.7 | 1.26 | 45 |
| 58 | Ph$_3$PO(30) | " | " | " | " | 1.7 | 1.26 | 50 |
| 59 | Ph$_3$PO(50) | " | " | " | " | 1.6 | 1.38 | 64 |
| 60 | Ph$_3$PO(100) | " | " | " | " | 1.7,1.7 | 1.53,1.44 | 65,62 |
| 61 | Ph$_3$PO(150)[b] | " | " | " | " | 1.5 | 1.40 | 74 |
| 62 | Ph$_3$PO(150)[b] | CsOAc (1.3) | " | " | " | 1.6 | 1.31 | 77 |
| 63 | Bu$_3$PO(150) | " | " | " | " | 1.5 | 1.48 | 76 |
| 64 | — | CsOAc (0.85) | " | " | " | ~1.1,~1.4 | 0.92,1.08 | 38,48 |
| 65 | Ph$_3$PO(100) | " | " | " | " | 1.5 | 1.46 | 73 |

[a]Scaled proportionally to 6 mmoles of rhodium dicarbonylacetylacetonate. Based on 75 ml of solvent.
[b]60 ml 18-crown-6.
[1]CsOAc - Cesium acetate
PhCO$_2$Cs - Cesium benzoate
Me$_2$CHCO$_2$Cs - cesium isobutyrate
[2]Ph$_3$PO - triphenylphosphine oxide
Bu$_3$PO - tributylphosphine oxide The Procedure was exactly repeated except that 75 ml. of 18-crown-6 was used as a solvent and the reaction time was 135 minutes. The data of Table V show that in 18-crown-6 (Examples 43 to 63) and 15-crown-5 (Examples 64 to 65) solvents at a pressure of 8000 psi, the addition of phosphine oxide to the reaction results in improvement in rate of formation of ethylene glycol and increased rhodium recovery.

EXAMPLES 66 TO 85

The Procedure was exactly repeated except that the reaction time was 135 minutes and the volume of 18-crown-6 solvent used is as indicated in Table VI.

The data of Table VI show the use of several phosphine oxides as a promoter/solvent.

TABLE VI

| Ex. | Phosphine Oxide[1] | (mmoles) | (Wt. %) | Salt (mmoles)[2] | Amine (mmoles) | Temp (°C) | 18-crown-6 Solvent, ml. | Rate,[a]Mhr$^{-1}$ Methanol | Ethylene glycol | % Rh Recovered |
|---|---|---|---|---|---|---|---|---|---|---|
| 66 | — | — | — | CsOAc(0.85) | N-methylmorpholine(7) | 270 | 75 | ~1.7,1.7 | 1.12,1.16 | 56,51 |
| 67 | Bu$_3$PO | 100 | | " | " | 270 | 75 | ~1.0 | 1.35 | 55 |
| 68 | Ph$_3$PO | 100 | | " | " | 270 | 75 | 1.7,1.7 | 1.53,1.44 | 65,62 |
| 69 | Me$_3$PO | 100 | | " | " | 270 | 75 | 1.5 | 1.65 | 78 |
| 70 | Ph$_3$PO | 150 | | " | " | 270 | 60 | 1.5 | 1.40 | 74 |
| 71 | Me$_3$PO | 150 | | " | " | 270 | 60 | 1.5 | 1.56 | 83 |

TABLE VI-continued

| Ex. | Phosphine Oxide[1] | (mmoles) | (Wt. %) | Salt (mmoles)[2] | Amine (mmoles) | Temp (°C) | 18-crown-6 Solvent, ml. | Rate,[a] Mhr$^{-1}$ Methanol | Ethylene glycol | % Rh Recovered |
|---|---|---|---|---|---|---|---|---|---|---|
| 72 | Me₃PO | 300 | | " | " | 270 | 60 | 1.2 | 1.27 | 94 |
| 73 | Ph₃PO | | 10 | " | " | 270 | 75 | 1.7 | 1.26 | 50 |
| 74 | Me₃PO | | 10 | " | " | 270 | 75 | 1.5 | 1.65 | 78 |
| 75 | Ph₃PO | | 14 | " | " | 270 | 75 | 1.6 | 1.38 | 64 |
| 76 | Me₃PO | | 17 | " | " | 270 | 60 | 1.5 | 1.56 | 83 |
| 77 | Ph₃PO | | 24 | " | " | 270 | 75 | 1.7,1.7 | 1.53,1.44 | 65,62 |
| 78 | Me₃PO | | 29 | " | " | 270 | 60 | 1.2 | 1.27 | 94 |
| 79 | Me₃PO | 150 | 14 | " | " | 280 | 75 | 2.0 | 1.88 | 82 |
| 80 | Ph₃PO | 100 | | CsOAc(1.5) | " | 270 | 75 | 2.2 | 1.19 | 76 |
| 81 | Ph₃PO | 150 | | CsOAc(1.3) | " | 270 | 60 | 1.6 | 1.31 | 77 |
| 82 | Bu₃PO | 150 | | " | " | 270 | 75 | 1.5 | 1.48 | 76 |
| 83 | Ph₃PO | 100 | | CsOAc(1.5) | N-methylmorpholine(7) | 270 | 75[b] | 1.5 | 1.41 | 77 |
| 84 | Ph₃PO | 150 | | CsOAc(1.3) | " | 270 | 60[b] | 1.5 | 1.25 | 85 |
| 85 | Bu₃PO | 150 | | " | " | 270 | 75[b] | 1.5 | 1.55 | 75 |

[a] Scaled proportionately to 6 mmoles of rhodium dicarbonylacetylacetonate. Based on 75 ml of solvent.
[b] Indicates the use of 15-crown-5 solvent
[1] Bu₃PO - tributylphosphine oxide
Ph₃PO - triphenylphosphine oxide
Me₃PO - trimethylphosphine oxide
[2] CsOAc - cesium acetate

EXAMPLES 86 TO 90

The Procedure was exactly repeated except that the amount of solvent indicated was used in Examples 87 to 90. Also, tripropylphosphine oxide in the amount indicated in Table VII was used.

TABLE VII

| Ex. | Tripropylphosphine Oxide (mmoles) | Salt(mmoles)[1] | Amine(mmoles) | Temp (°C.) | Pressure (psig) | 18-crown-6 Solvent, ml. | Rate,[a] Mhr$^{-1}$ Methanol | Ethylene glycol | % Rh Recovered |
|---|---|---|---|---|---|---|---|---|---|
| 86 | — | CsOAc (0.85) | N-methylmorpholine(7) | 270 | 8,000 | 75 | ~1.7,1.7 | 1.12,1.16 | 56,51 |
| 87 | 150 | CsOAc (0.85) | N-methylmorpholine(7) | 270 | 8,000 | 60 | 1.5 | 1.72 | 69 |
| 88 | 300 | " | " | " | " | 30 | 1.4 | 2.06 | 72 |
| 89 | 300 | CsOAc (1.3) | " | " | " | 30 | 2.1 | 1.99 | 75 |
| 90 | 300 | CsOAc (0.85) | " | " | " | 15 | 1.9 | 1.87 | 56 |

[a] Scaled proportionately to 6 mmoles of rhodium dicarbonylacetylacetonate
[1] CsOAc - cesium acetate

EXAMPLES 91 TO 102

The Procedure was exactly repeated. The results in Table VIII illustrates the use of an alkoxyalkylene phosphine oxide.

TABLE VIII

| Example | Phosphine Oxide (mmoles) | Salt (mmoles)[1] | Amine (mmoles) | Solvent | Temp. (°C.) | Wt. of Product Methanol (g) | Ethylene Glycol(g) | % Rh Recovered |
|---|---|---|---|---|---|---|---|---|
| 91 | — | HCO$_2$Cs(0.5) | — | sulfolane | 240 | 4.07 | 1.50 | 72 |
| 92 | (CH$_3$CH$_2$CH$_2$OCH$_2$)$_2$P(O)CH$_3$(2.5) | " | — | " | " | 4.22 | 2.49 | 77 |
| 93 | — | HCO$_2$Cs(0.65) | — | sulfolane | 240 | 3.75 | 3.65 | 80 |
| 94 | (CH$_3$OCH$_2$CH$_2$OCH$_2$)$_2$P(O)CH$_3$(3.25) | " | — | " | " | 2.06 | 4.45 | 72 |
| 95 | (CH$_3$OCH$_2$CH$_2$OCH$_2$)$_2$P(O)CH$_3$(10.0) | " | — | " | " | 2.12 | 4.00 | 74 |
| 96 | — | HCO$_2$Cs(0.65) | — | sulfolane | 250 | 4.40 | 4.70 | 65 |
| 97 | — | HCO$_2$Cs(0.65) | — | sulfolane | 250 | 3.86 | 4.70 | 61 |
| 98 | (CH$_3$CH$_2$CH$_2$OCH$_2$)$_2$P(O)CH$_3$(3.25) | HCO$_2$Cs(0.65) | Pyridine (1.25) | tetraglyme | 220 | 2.83,1.95 | 4.41,4.11 | 85,83 |
| 99 | — | " | " | sulfolane | " | 2.90 | 1.54 | 91 |
| 100 | see solvent column | " | " | (CH$_3$OCH$_2$CH$_2$OCH$_2$)$_2$P(O)CH$_3$ | " | 1.00 | 3.80 | 83 |
| 101 | — | HCO$_2$Cs(0.5) | Pyridine (1.25) | tetraglyme | 220 | 2.19 | 3.06 | 80 |
| 102 | (CH$_3$OCH$_2$CH$_2$OCH$_2$)$_2$P(O)CH$_3$(2.5) | " | " | " | " | 2.97 | 2.45 | 94 |

[1]HCO$_3$Cs - cesium formate

What is claimed is:

1. The process for producing polyhydric alcohol(s) which comprises converting a mixture consisting essentially of hydrogen and oxide of carbon to said polyhydric alcohol(s) by reacting said mixture in a homogeneous liquid phase containing a rhodium carbonyl complex and a phosphine oxide compound(s) which phosphine oxide compound(s) is free of sulfur atoms and halogen atoms other than fluorine, at a temperature of between about 100° C. and 375° C. and a pressure of between about 1000 psia. and 50,000 psia. sufficient to produce said polyhydric alcohol(s).

2. The process of claim 1 wherein the reaction is effected at a temperature of between about 150° C. and 350° C.

3. The process of claim 2 wherein the reaction is effected at a temperature of between about 190° C. and 320° C.

4. The process of claim 1 wherein the reaction is effected at a pressure of between about 1000 psia. and 25,000 psia.

5. The process of claim 4 wherein the reaction is effected at a pressure of between about 1000 psia. and 17,000 psia.

6. The process of claim 1 wherein the homogeneous liquid phase contains an organic solvent.

7. The process of claim 6 wherein the solvent is a tetramethylene sulfone.

8. The process of claim 7 wherein the solvent is sulfolane.

9. The process of claim 7 wherein the solvent is 3,4-bis(2-methoxyethoxy)sulfolane.

10. The process of claim 6 wherein the solvent is tetraglyme.

11. The process of claim 6 wherein the solvent is a crown ether.

12. The process of claim 11 wherein the crown ether is [18]-crown-6.

13. The process of claim 11 wherein the crown ether is [15]-crown-5.

14. The process of claim 1 wherein the reaction is effected in the presence of at least one of a Lewis base nitrogen compound or a salt.

15. The process of claim 14 wherein the salt is at least one of an alkali metal hydroxide, halide, alkoxide and carboxylate salt.

16. The process of claim 15 wherein the salt is a carboxylate salt.

17. The process of claim 16 wherein the salt is a cesium carboxylate.

18. The process of claim 16 wherein the salt is a potassium carboxylate.

19. The process of claim 17 wherein the salt is cesium p-methylsulfonylbenzoate.

20. The process of claim 17 wherein the salt is cesium formate.

21. The process of claim 17 wherein the salt is cesium benzoate.

22. The process of claim 17 wherein the salt is cesium acetate.

23. The process of claim 18 wherein the salt is potassium benzoate.

24. The process of claim 16 wherein the salt is ammonium benzoate.

25. The process of claim 14 wherein the Lewis base nitrogen compound is an amine.

26. The process of claim 25 wherein the amine is pyridine.

27. The process of claim 25 wherein the amine is N-methylmorpholine.

28. The process of claim 25 wherein the amine is a dimorpholine.

29. The process of claim 28 wherein the dimorpholine is ethylenedimorpholine.

30. The process of claim 1 wherein the phosphine oxide is triarylphosphine oxide.

31. The process of claim 30 wherein the triaryl phosphine oxide is triphenylphosphine oxide.

32. The process of claim 1 wherein the phosphine oxide is trialklyphosphine oxide.

33. The process of claim 32 wherein the trialkylphosphine oxide is trimethylphosphine oxide.

34. The process of claim 32 wherein the trialkylphosphine oxide is tripropylphosphine oxide.

35. The process of claim 32 wherein the trialkylphosphine oxide is tributylphosphine oxide.

36. The process of claim 1 wherein the phosphine oxide is an alkoxyalkylene phosphine oxide.

37. The process of claim 36 wherein the alkoxyalkylene phosphine oxide is $(CH_3OCH_2CH_2OCH_2)_2P(O)CH_3$.

* * * * *